(12) United States Patent
Mathieu et al.

(10) Patent No.: US 7,641,676 B2
(45) Date of Patent: Jan. 5, 2010

(54) IMPLANT FOR FIXING BONES

(75) Inventors: Claude Mathieu, Bettlach (CH); Robert Frigg, Bettlach (CH); Marco Spichiger, Grenchen (CH); Beat Lechmann, Bettlach (CH)

(73) Assignee: Synthes USA, LLC, West Chester, PA (US)

( * ) Notice: Subject to any disclaimer, the term of this patent is extended or adjusted under 35 U.S.C. 154(b) by 608 days.

(21) Appl. No.: 10/536,509

(22) PCT Filed: Dec. 2, 2002

(86) PCT No.: PCT/CH02/00650

§ 371 (c)(1),
(2), (4) Date: Jun. 24, 2005

(87) PCT Pub. No.: WO2004/049962

PCT Pub. Date: Jun. 17, 2004

(65) Prior Publication Data

US 2006/0079900 A1 Apr. 13, 2006

(51) Int. Cl.
*A61B 17/80* (2006.01)
(52) U.S. Cl. .............. 606/298; 606/287; 606/301
(58) Field of Classification Search ............ 606/61, 606/69, 70, 71, 72, 73, 77, 291, 287, 281, 606/298, 301
See application file for complete search history.

(56) References Cited

U.S. PATENT DOCUMENTS

| | | | | |
|---|---|---|---|---|
| 5,108,399 A | * | 4/1992 | Eitenmuller et al. | 606/77 |
| 5,269,784 A | * | 12/1993 | Mast | 606/288 |
| 5,578,034 A | * | 11/1996 | Estes | 606/61 |
| 5,976,141 A | * | 11/1999 | Haag et al. | 606/292 |
| 6,004,323 A | | 12/1999 | Park et al. | |
| 6,206,881 B1 | * | 3/2001 | Frigg et al. | 606/291 |
| 6,955,677 B2 | * | 10/2005 | Dahners | 606/287 |
| 2001/0021851 A1 | * | 9/2001 | Eberlein et al. | 606/69 |
| 2002/0082603 A1 | * | 6/2002 | Dixon et al. | 606/69 |

FOREIGN PATENT DOCUMENTS

| | | |
|---|---|---|
| DE | 1 949 923 | 4/1971 |
| FR | 2 726 461 | 5/1996 |
| GB | 1 300 449 | 12/1972 |

OTHER PUBLICATIONS

WO 03/055401, Device for Performing Osteosynthesis, Publication Date Jul. 10, 2003.

* cited by examiner

*Primary Examiner*—Pedro Philogene
(74) *Attorney, Agent, or Firm*—Stroock & Stroock & Lavan LLP

(57) ABSTRACT

An implant for use in bone fixation, includes combination of the two materials: metal and plastic. The implant defines several passages with axles (3) running through the implant, which are suitable for receiving a bone fixation device, such as a bone screw. The passages are provided with a peripheral perimeter, which is made of a different materiel than the material of the implant surrounding the perimeter. The implant is, on the one hand, not too rigid and, on the other hand, does not present problems as regards the screw-implant interface.

8 Claims, 3 Drawing Sheets

IMPLANT FOR FIXING BONES

The invention relates to an implant for use in bone fixation, specifically a bone plate according to the generic term of Patent Claim 1.

Bone plates made either of metals or metal alloys or of plastic materials, specifically resorbable polymers, are already state of the art. Metallic bone plates are, however, either too rigid, and the less rigid plastic plates, specifically plates made of resorbable plastics, do not provide the necessary strength. In addition, problems also occur when plastic plates are joined to metallic bone screws, specifically the joints in such cases are not always sufficiently stable.

The invention is intended to remedy this situation. The invention is based on the task of creating an implant that is, on the one hand, not too rigid and, on the other hand, does not present problems as regards the screw-implant interface.

The invention solves the set task by providing an implant with the features of claim 1.

In one embodiment of the implant, the perimeter is ring-shaped or sleeve-shaped. The external form of the perimeter can, however, also be designed with a polygonal, e.g. rectangular, shape.

The implant is preferably formed as a bone plate, with a bottom side and an upper side suitable for the bone contact, wherein the passages connect the upper side with the bottom side.

The perimeter is preferably made of a metal or a metal alloy and the material surrounding the perimeter is preferably a plastic. In this way, the plate will not have to bear the same load. The plate is also less rigid, which leads to improved healing of the bone in accordance with Wolff's law, and finally it is also less radio opaque, which means that less artifacts appear in the x-ray pictures, CT or MRI, which in turn allows enhanced monitoring of the healing process.

The perimeter can, however, also be made of a plastic, and the material surrounding the perimeter can be a metal or a metal alloy.

Suitable plastics are above all PEEK or some related polymers from the Polyaryletherketone (PAEK) family. The plastic can moreover also be reinforced, e.g. with carbon fibres or PEEK fibres.

Suitable metals are, for example, titanium, titanium alloys or implant steel.

The elements of the implant made of plastic are preferably covered with a coating of titanium or a Hydroxylapatite layer. The advantage of such coating is that it prevents all direct contact between metal and bone, while at the same time achieving the same surface as with a metal plate, but nevertheless has the mechanical features of a plastic.

In a special embodiment, the perimeter is provided with a sleeve-shaped extension suitable as a target aid for a bone fixation device. The extension can be formed on the perimeter and both—perimeter and sleeve-shaped extension—are preferably made of plastic.

One particularly simple realisation of the implant is when the perimeter is made of metal or a metal alloy and is set lowered in the plastic surrounding the perimeter, vis-à-vis the upper side. Alternately, the perimeter can be set higher in the surrounding plastic, vis-à-vis the upper side.

The level containing or lying on the perimeter can in one embodiment form an angle in the range 0.1° to 20.0° to the plate level, so that the passages (or the axles of the passages) will then also be able to form such an angle vis-à-vis the verticals on the plate level.

In one embodiment, the implant—specifically when this entails a bone plate—is provided with at least two passages running through the implant, which are suitable for receiving a bone fixation device, specifically a bone screw.

In a further embodiment, at least two of the passages running through the implant are provided with a peripheral perimeter that is made of a different material than the implant material surrounding the perimeter.

The peripheral perimeters will then preferably be linked to each other in one piece by several passages running through the implant, which allows both simple manufacture of the implant and improved anchoring of the perimeters in the surrounding plastic material.

In a further embodiment, the peripheral perimeters are securely linked to the implant. This results in enhanced stability and simplified handling of the implant compared to removable peripheral perimeters.

When there are several peripheral perimeters, these can also be joined together in the form of a grid.

The implant can be fixed to the bone to be treated by means of suitable bone fixation devices that can be inserted into the passages, preferably in the form of bone screws. The bone screws can be inserted in mono-axial or poly-axial direction in relation to the implant. The connection of the bone screws to the implant can be carried out either with a stable or non-stable angle.

The invention and derived forms of the invention shall be described in more detail in the following on the basis of a partially schematic representation of several embodiments.

Figure 1:
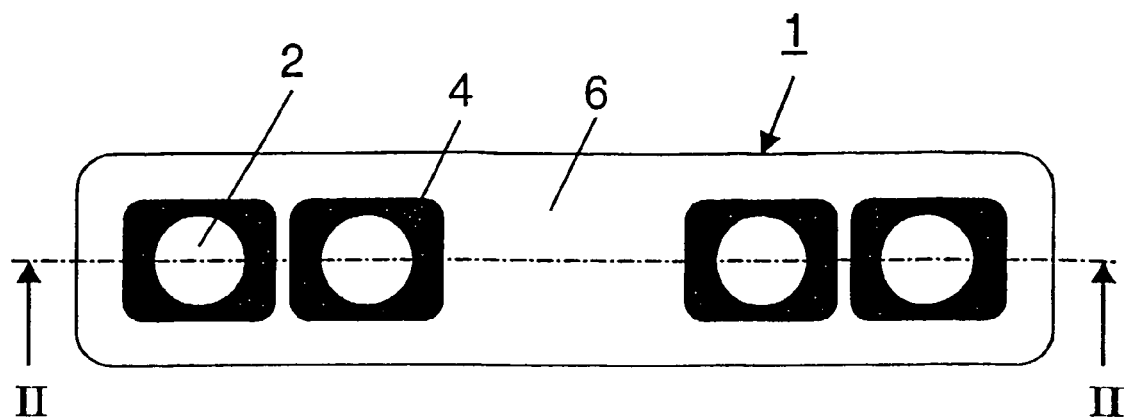
FIG. 1 shows an overview view of a bone plate made of plastic with four plate drill holes, with a metallic, rectangular perimeter.
Figure 2:
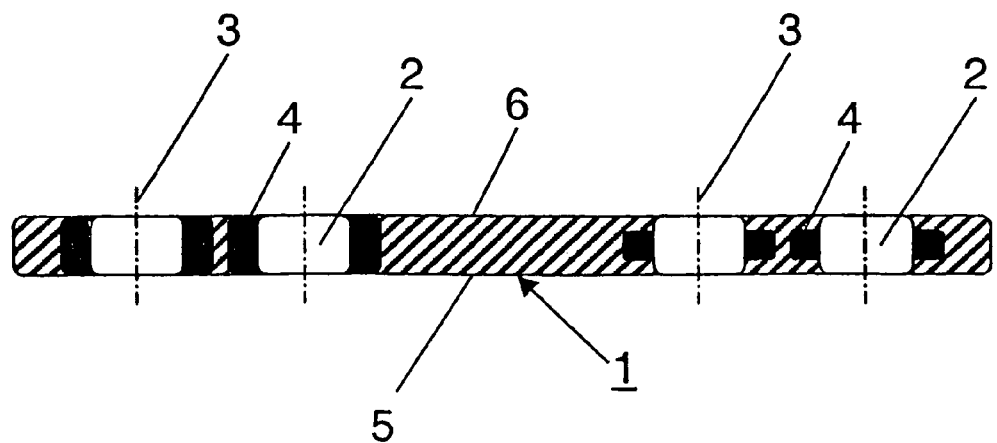
FIG. 2 shows a longitudinal section through the bone plate according to FIG. 1 along the line II-II.

The implant 1 illustrated in FIG. 1 and FIG. 2 is a bone plate, the main element of which consists of bio-compatible plastic, e.g. Polyetheretherketone (PEEK), and which is provided with four passages 2 in the form of circular holes with the axle 3 for receiving bone screws (not shown in the illustration). The passages 2 connect the bottom side 5 of the bone plate suitable for attachment to the bone to its upper side 6.

The passages 2 are provided in the form of rectangular dies made of metal, which can be designed as perimeters 4 of the passages 2. The perimeters 4, which can for example be made of titanium, are worked into the surrounding plastic material 7 (e.g. PEEK) in spray cast according to their manufacture and are connected with positive fit to the plastic material 7.

A variation of the insertion of the perimeter 4 in the plastic material 7 is shown on the right side of FIG. 2, in which the metallic dies are set less high than on the left side of FIG. 2, so that they are set lowered vis-a-vis the upper side 6 and the bottom side 5, and are therefore surrounding by plastic material 7.

Figure 4:
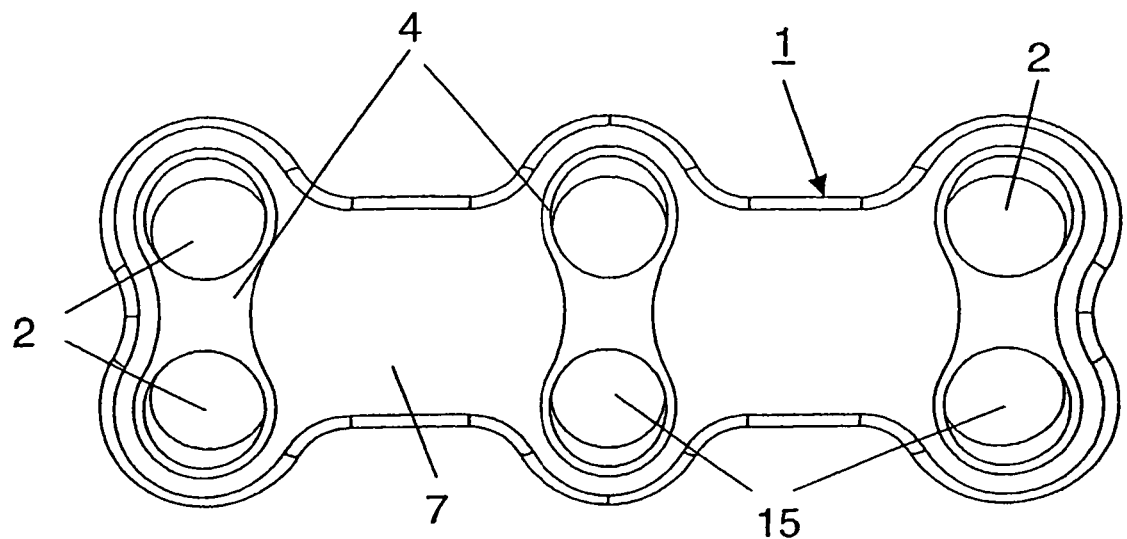
FIG. 4 shows an overview on the bone plate according to FIG. 3.
Figure 3:
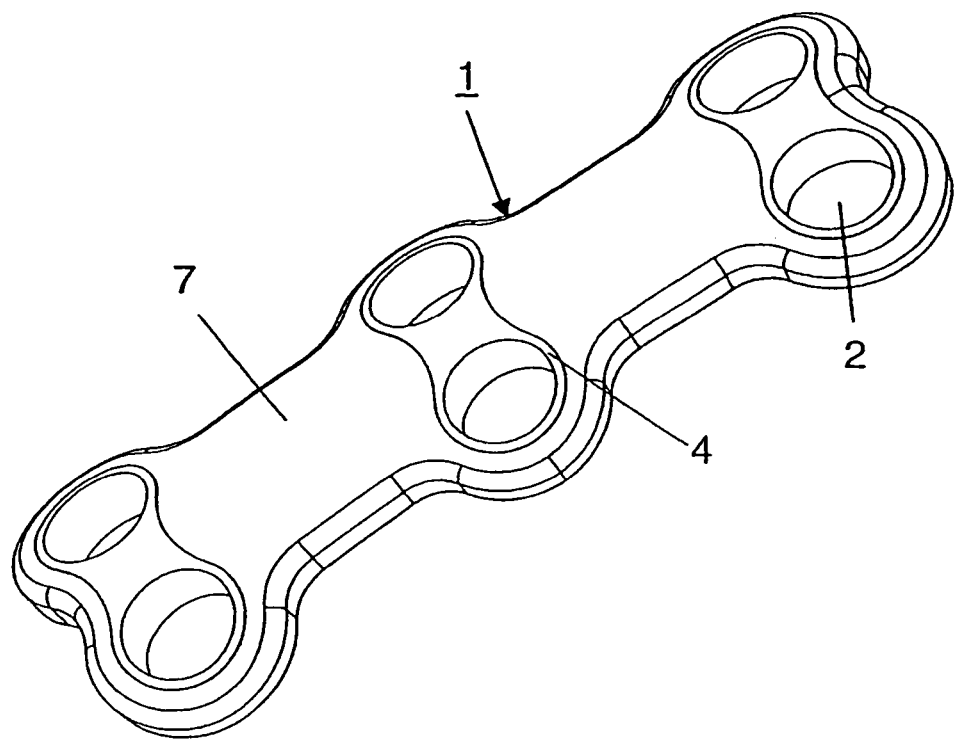
FIG. 3 shows a perspective view of a modified bone plate with sleeve-shaped perimeters.

In another embodiment shown in FIG. 3 and FIG. 4, the implant 1 is also a bone plate. This is made of PEEK, which is reinforced with PEEK fibres. In contrast to the embodiment in accordance with FIG. 1 and FIG. 2, two perimeters 4 made of titanium are joined together as one piece in each case and set into the surrounding PEEK material 7 as spray cast in its entirety. The external form of the different perimeters 4 is thereby circular or sleeve-shaped.

Figure 5:
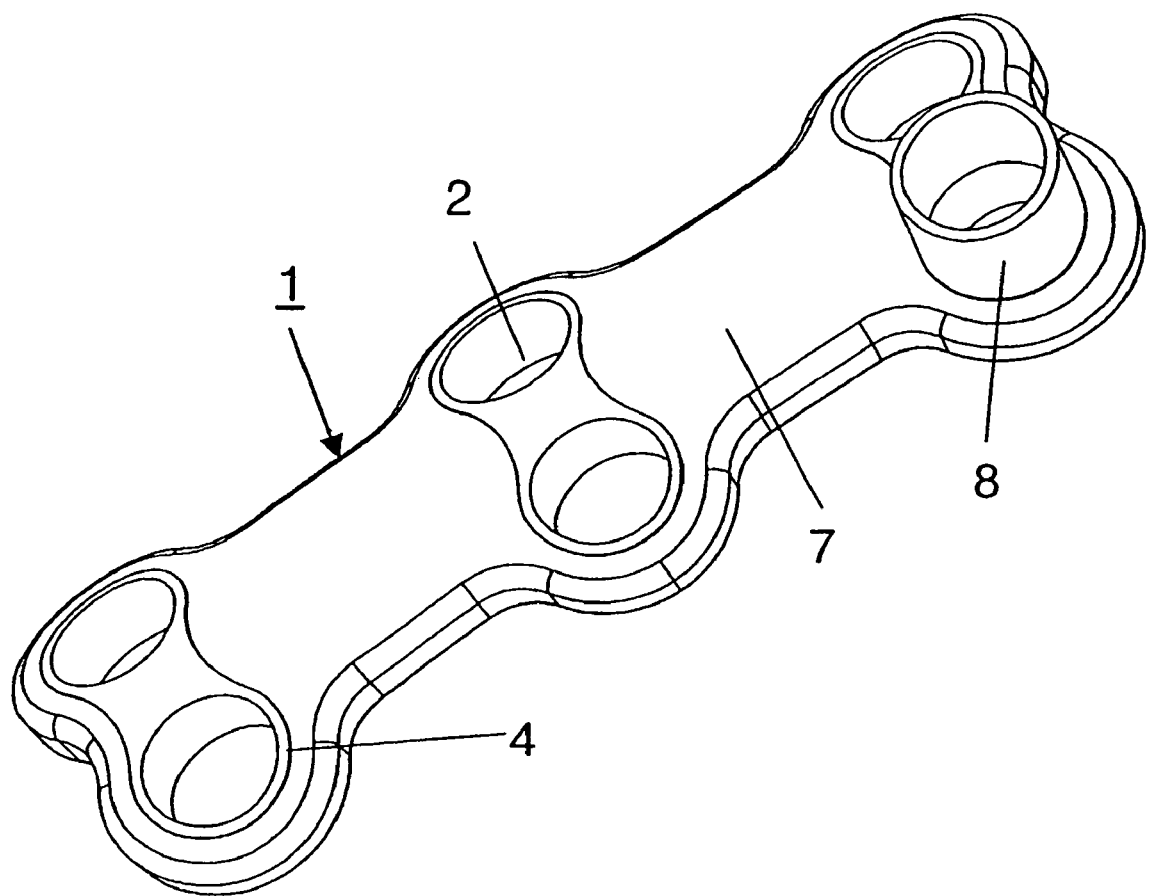
FIG. 5 shows a perspective view of a modified bone plate with a sleeve-shaped extension on one of the plate holes.

In the case of a modification shown in FIG. 5, a sleeve-shaped extension 8 is formed on one of the perimeters 4 that is suitable as target aid for a bone fixation device, e.g. a bone screw.

The invention claimed is:

1. An implant for bone fixation comprising:
   a body having an upper surface and a bottom surface wherein the body is formed of a plastic material;
   a first openings extending from the upper surface through to the bottom surface, a second opening extending from the upper surface through to the bottom surface each of which opening is configured to receive a bone fastener;
   a passage located between the first opening and second opening the passage extending through the upper surface;
   a first peripheral perimeter formed of titanium material; and
   a second peripheral perimeter formed of titanium material;
   wherein the first and second peripheral perimeters are joined together as a single piece and rigidly inserted within the first and second openings and the passage.

2. The implant in accordance with claim 1, wherein the first peripheral perimeter has a polygonal external form.

3. The implant in accordance with claim 1, wherein the plastic material is chosen from the Polyaryletherketone (PEEK) family.

4. The implant in accordance with claim 1, wherein PEEK is used as the plastic material.

5. The implant in accordance with claim 1, wherein the plastic material is reinforced with a reinforcing material selected from the group consisting of carbon fibers and PEEK fibers.

6. The implant in accordance with claim 1, wherein the plastic material is covered with a coating, said coating being selected from the group consisting of titanium and Hydroxylapatite.

7. The implant in accordance with claim 1, wherein a level containing or laid on the first peripheral perimeter has an angle in the range 0.1° to 20.0° to the body level.

8. An implant for bone fixation comprising:
   a body having an upper surface and a bottom surface wherein the body is formed of a plastic material;
   a first openings extending from the upper surface through to the bottom surface, a second opening extending from the upper surface through to the bottom surface each of which opening is configured to receive a bone fastener;
   a passage located between the first opening and second opening the passage extending through the upper surface;
   a first peripheral perimeter formed of titanium material and containing a sleeve shaped extension; and
   a second peripheral perimeter formed of titanium material;
   wherein the first and second peripheral perimeters are joined together and rigidly inserted within the first and second openings and the passage and wherein the sleeve shaped extension is located above the upper surface of the body and acts as a target aid for the respective bone fastener.

* * * * *